(12) United States Patent
Rosengren

(10) Patent No.: US 6,593,755 B1
(45) Date of Patent: Jul. 15, 2003

(54) METHOD AND APPARATUS FOR DETECTION SENSOR SHIELDING

(75) Inventor: Brian P. Rosengren, Eden Prairie, MN (US)

(73) Assignee: Banner Engineering Corporation, Minneapolis, MN (US)

( * ) Notice: Subject to any disclaimer, the term of this patent is extended or adjusted under 35 U.S.C. 154(b) by 310 days.

(21) Appl. No.: 09/628,711

(22) Filed: Jul. 31, 2000

(51) Int. Cl.$^7$ .............................................. G01R 27/26
(52) U.S. Cl. ...................................... 324/677; 324/662
(58) Field of Search ................................ 324/627–628, 324/658–724, 609–611, 647–648; 340/561–563, 870.37; 343/841; 701/45; 280/735

(56) References Cited

U.S. PATENT DOCUMENTS

| | | | |
|---|---|---|---|
| 3,896,425 A | 7/1975 | Erichsen | 340/563 |
| 4,661,797 A | 4/1987 | Schmall | 340/561 |
| 4,914,421 A | 4/1990 | d'Alayer de Costemore d'Arc et al. | 369/53.41 |
| 5,166,679 A | 11/1992 | Vranish et al. | 340/870.37 |
| 5,214,388 A | 5/1993 | Vranish et al. | 324/683 |
| 5,373,245 A | 12/1994 | Vranish | 324/662 |
| 5,442,347 A | 8/1995 | Vranish | 340/870.37 |
| 5,539,292 A | 7/1996 | Vranish | 318/568.21 |
| 5,650,730 A | 7/1997 | Herbst, Jr. | 324/690 |
| 5,726,581 A | 3/1998 | Vranish | 324/688 |
| 5,730,165 A | 3/1998 | Philipp | 137/1 |
| 5,793,217 A | 8/1998 | Herbst, Jr. | 324/690 |
| 6,392,542 B1 | 5/2002 | Stanley | 340/561 |
| 2001/0045733 A1 * | 11/2001 | Stanley et al. | 280/735 |

FOREIGN PATENT DOCUMENTS

DE 195 21 129 C1 10/1996
DE 19521129 * 10/1996 ............ G01D/5/24

OTHER PUBLICATIONS

"Con–Tech", "CS2000 Features", http://con–tech.com/features_cp.htm, last updated Oct. 16, 2000 (we were aware of this website on or about Aug. 24, 2000).

"Con–Tech", "CS2000–QD Label Sensor", http://con–tech.com./cs2000qd_cp.htm, last updated Oct. 16, 2000 (we were aware of this website on or about Aug. 24, 2000).

"Quantum Research Group Ltd", "Creating a sensor of achievement", *Focus*, (Jan. 1998), http://interquant.com/patents.htm, last updated Jul. 12, 1999.

"All Label", "All Label Sees all, detectsall!", *Rechner*, Ed. No. 12, http://www.rechner–sensors.de/alllabgb.htm, last updated Jul. 12, 1999.

"Lion Precision", "LRD2100 Label Edge Detection System", *Label Detection Systems*, http://www.lionprecision.com/label/index.html, last updated Jul. 12, 1999.

Marko et al., entitled Method and Apparatus for Detection Signal Processing, filed Jul. 31, 200, Ser. No. 09/629,499.

* cited by examiner

*Primary Examiner*—Christine Oda
*Assistant Examiner*—John Teresinski
(74) *Attorney, Agent, or Firm*—Merchant & Gould

(57) ABSTRACT

A system and method are disclosed for shielding a capacitive sensor. The system and method drive the shield to the same potential as the sensor electrode being shielded to eliminate sensor interference due to mutual capacitance. An independently created signal is applied to the shield which matches the signal applied to the sensor electrode. Use of the independent driving signal allows the shield to maintain the same potential as the sensor electrode, especially during rapid transition of the sensor electrode's potential.

15 Claims, 19 Drawing Sheets

METHOD AND APPARATUS FOR DETECTION SENSOR SHIELDING

TECHNICAL FIELD

The present invention relates to a method and apparatus for shielding a sensor device. More specifically, the present invention relates to shielding a capacitive-type sensor.

BACKGROUND

Detection devices determine when a particular event occurs. Examples of detection devices include beam sensors such as those used in automatic doors. The beam sensor determines when a person has approached the door by detecting when the beam has been reflected or broken. Once the person is detected by the sensor, the door is automatically opened for the user. Other examples include label sensors. Label sensors detect labels as they pass by the sensor on a web. The detection of the label allows proper high-speed counting of labels as well as proper removal of the labels from the web.

For a detection device to properly function, it must be shielded from interference that may influence the detection device's operation. In the case of capacitive type sensors, the sensor electrode must be isolated from undesired ground surfaces because the sensor is intended to measure the capacitance between a sensor electrode and ground electrode and undesired ground surfaces affect that capacitance value. Objects moving in proximity to the sensor and the undesired ground surfaces will change the capacitance between the sensor electrode and the ground surfaces which may result in a false sensing condition. To reduce the effects of the undesired ground surfaces, a shield is provided to surround the sensor electrode except on the side facing the ground electrode. However, the shield itself may act as an undesired ground surface that influences the signal applied to the sensor and may cause false sensing conditions to occur.

SUMMARY

The present invention addresses these problems by driving the shield to a potential matching the potential of the sensor electrode. The driving signal is independently created which allows the potential of the shield to closely match the potential of the sensor electrode during periods when the sensor electrode's potential is varying rapidly.

The invention is embodied in apparatuses and methods for providing a capacitive-type label sensor for sensing an object where the sensor has a reference electrode coupled to a first side of an opening and a sensor electrode coupled to a second side of the opening. The method includes electrically connecting the reference electrode to system ground and electrically connecting the sensor electrode to a first end of a first resistor and a first electronic driving circuit at a first connection where the first resistor is electrically coupled between the first connection and a supply voltage. The method also includes electrically connecting a shield electrode to a first end of a second resistor and a second electronic driving circuit at a second connection where the second resistor is electrically coupled between the second connection and the supply voltage. The method further includes determining the edge of the object passing through the opening by detecting a change in capacitance between the sensor electrode and the reference electrode.

The apparatus includes a reference plate coupled to the first side of the opening that is electrically connected to ground and includes a first electronic driving circuit for generating an output signal related to the measured capacitance within the opening. Also included in the apparatus is a sensor electrode coupled to the second side of the opening and electrically connected to the first electronic driving circuit at a first connection. A first resistor is included and is electrically connected between the first connection and a supply voltage. The apparatus further includes a second electronic driving circuit and includes a shield electrode coupled to the second side of the opening and electrically connected to the second electronic driving circuit at a second connection. A second resistor is included and is electrically connected between the second connection and the supply voltage. A low pass filter circuit is included and generates a capacitance signal from filtering the output signal.

DETAILED DESCRIPTION

Figure 1:
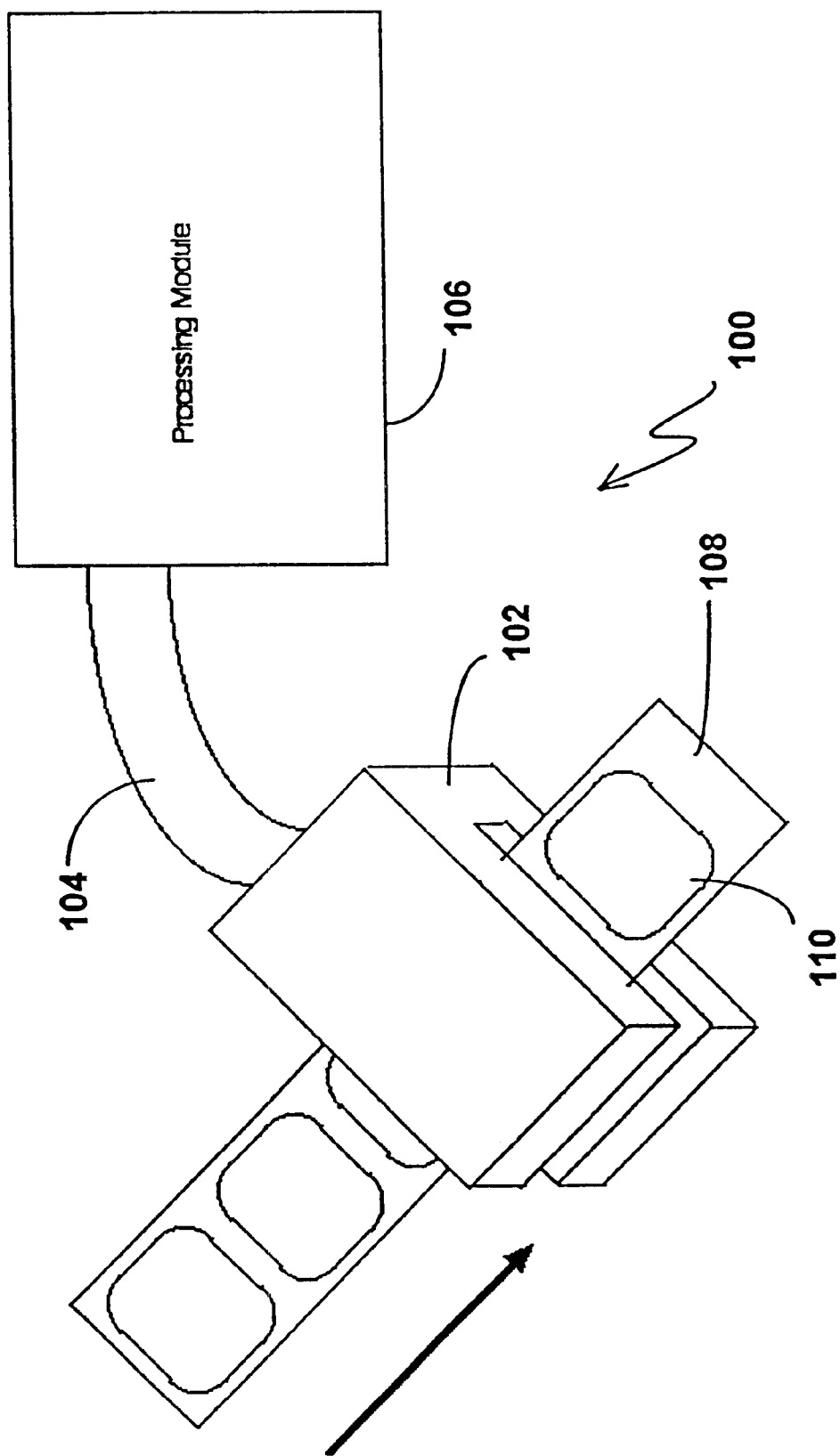
FIG. 1 illustrates a label web, sensor unit, and associated processing module.

Various embodiments of the present invention will be described in detail with reference to the drawings, wherein like reference numerals represent like parts and assemblies through the several views. Reference to various embodiments does not limit the scope of the invention, which is limited only by the scope of the claims attached hereto.

Several embodiments of the shielded detection sensor are described. These embodiments provide exemplary implementations of the process taken to shield the sensor electrode. These embodiments include a system that maintains the potential on the shield electrode at the same potential as the sensor electrode.

Although the exemplary embodiments are directed to capacitive type label sensors, many other capacitive sensor types can be implemented by the present invention and these sensors may be used for many purposes in addition to sensing label transitions. Other capacitive sensors and capacitive sensor applications that apply to this invention are well known in the art. Furthermore, the signal processing hardware and operations shown and described below to detect label transitions are for exemplary purposes only and other processing hardware and operations may be used with the shielded sensor.

With reference to FIG. 1, a basic capacitive type label sensor system 100 is shown. The system 100 includes a capacitive sensing unit 102 that receives the label web 108. Labels 110 are periodically spaced along the web 108. Typically, a feeding mechanism (not shown) supplies the label web 108 continuously to the sensing unit 102. The sensing unit 102 then feeds a sensed signal through communication cable 104 to a processing module 106 that interprets the signal to determine that a label is present.

Figure 2:
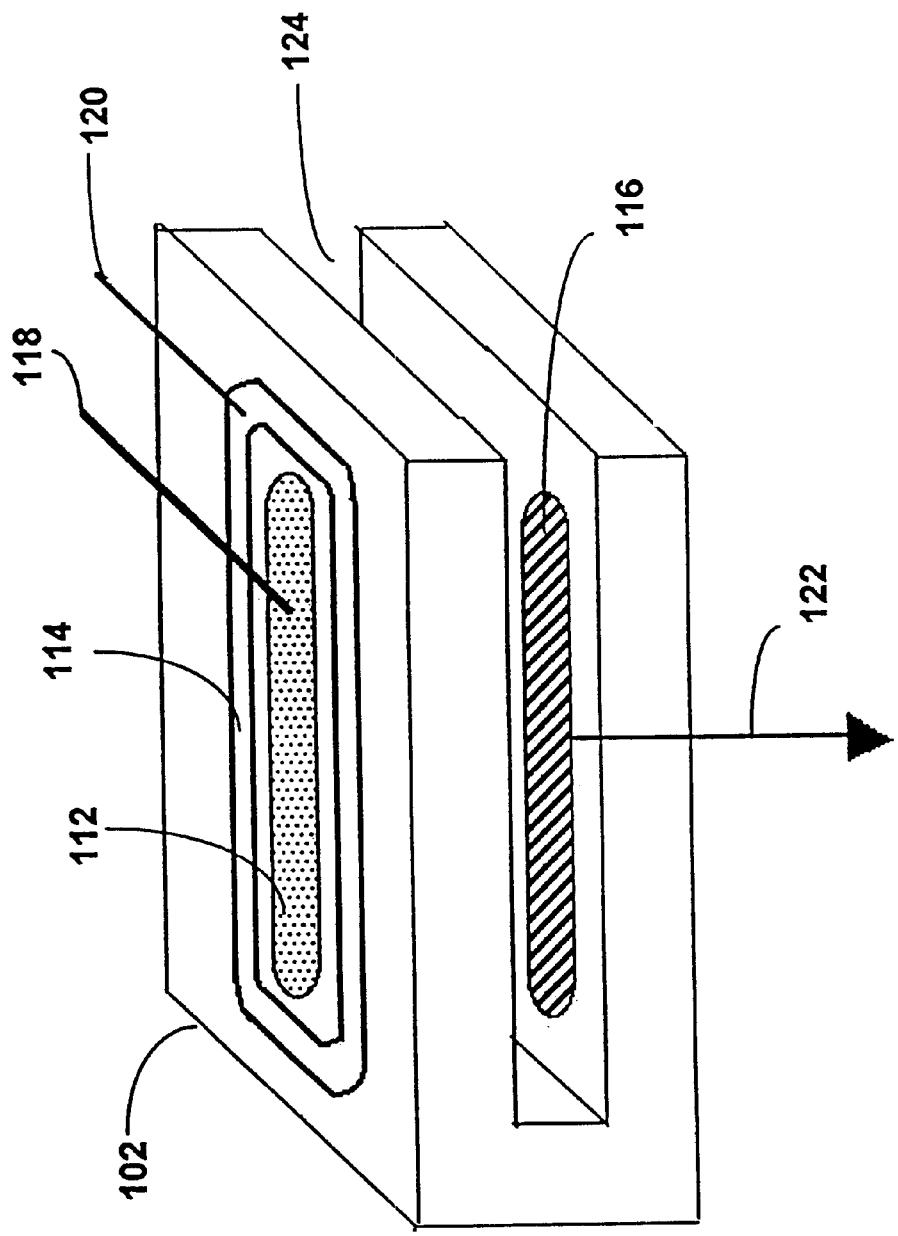
FIG. 2 shows the sensor unit's electrode configuration.

FIG. 2 illustrates some of the elements of the capacitive sensing unit 102. The sensing unit 102 includes a sensing electrode 112 that is surrounded by a shielding electrode 114. Though FIG. 2 illustrates the shielding electrode 114 surrounding the front, back, left, and right sides of the sensing electrode 112, the shielding electrode 114 will also cover the top of the sensing 112 as well. A reference electrode 116 is positioned across the gap or opening 124 from the sensing electrode 112, and the shielding electrode 114 and is connected to ground 122.

The sensing unit 102 also includes electrical connection 118 that leads from the sensor electrode 112 to processing circuitry used to detect events from the change in signal occurring at the sensor electrode 112. Electrical connection 120 leads from the shield electrode 114 to driving circuitry used to eliminate mutual capacitance between the sensor electrode 112 and shield electrode 114.

Figure 3:
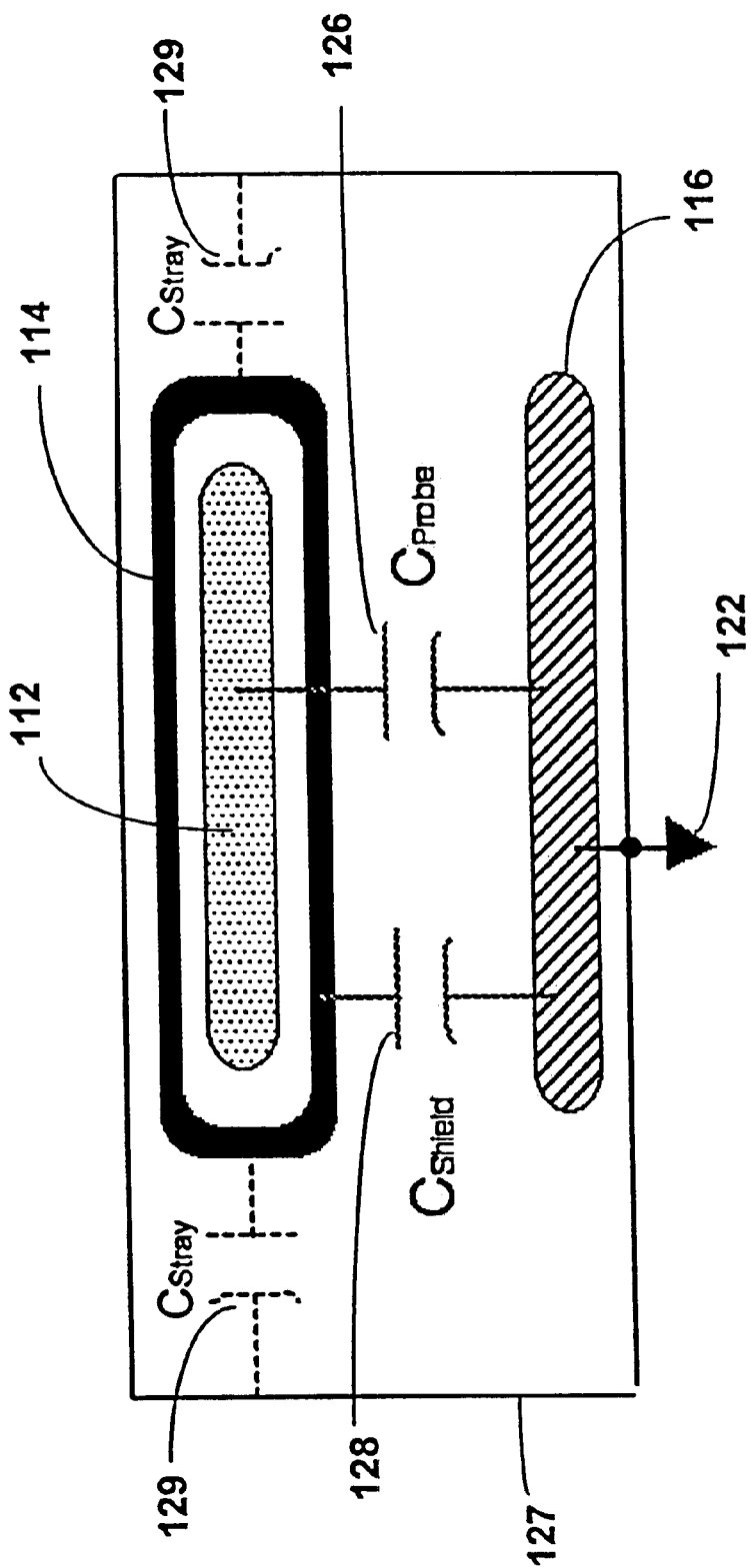
FIG. 3 depicts the sensor and shield capacitances.

FIG. 3. illustrates the effect of providing a sensing electrode and a shielding electrode. The separation of the sensing electrode 112 from the ground electrode 116 results in a capacitance 126 ($C_{Probe}$) which exists in the gap 124. A capacitance 128 ($C_{shield}$) exists in the gap 124 between the shielding electrode 114 and the ground electrode 116 and other undesired ground surfaces. $C_{shield}$ 128 differs from $C_{Probe}$ 126 because of the variance in the geometry and spacing of the shielding probe 114 from the ground probe 116 as compared to the geometry and spacing of the sensing probe 112 from the ground probe 116. Additionally, the capacitance experienced by the shield electrode 114 differs from $C_{probe}$ 126 because the shield electrode 114 experiences stray capacitance $C_{stray}$ 129 between itself and other undesired ground surfaces, such as a grounded metal housing 127 surrounding the electrodes. These additional capacitances are not experienced by the sensor electrode 112 due to the presence of the shielding electrode 114.

Driving the shielding electrode 114 with a voltage waveform having the same characteristics as the waveform applied to the sensor electrode 112 results in little or no mutual capacitance between the two electrodes. This effect is desirable because for proper label detection, the sensing electrode 112 must only be influenced by the material present in the gap. The electronics necessary for driving both the sensing electrode 112 and the shielding electrode 114 are described herein with reference to FIG. 4.

To sense the presence of a label or the label web, the sensing electrode 112 is periodically driven to a potential by the sensor electronics 130 through electrical conductor 118. The frequency of the voltage waveform is much greater than the highest frequency at which the labels will pass through the gap 124. This frequency is controlled by a system clock. A 2 MHz system clock resulting in a 2 MHz waveform is typical. The clock pulse is fed to a sensor dedicated monostable multivibrator 136 through line 140. The dedicated multivibrator 136 is also connected to line 118 which leads to the sensing electrode 112. Line 118 is also connected to a DC power source (not shown) through a resistor 138.

The multivibrator 136 discharges the capacitance 126 between the sensor electrode 112 and ground 116 upon receiving each clock pulse from line 140. The voltage at the sensing electrode 112 is reduced to ground potential or zero since the multivibrator completes a short to ground. The multivibrator then opens the discharge path and the voltage on the sensing electrode 112 begins to charge back toward the level of the DC power source. The rate of charge is governed by the time constant or product of the resistance of resistor 138 and the capacitance 126.

The capacitance 126 varies depending upon whether the label 110 is present in the gap or only the web 108 is present. If the label is present, the dielectric value increases which increases the capacitance. The resistance of resistor 138 stays the same so the time constant increases for the recharging of the potential on the sensing electrode 112. The multivibrator 136 produces an output pulse on line 104 whose width is determined by the rate at which the voltage recharges on the sensing electrode 112. Thus, the pulse width of the sensed signal output from the sensor unit 102 varies in proportion to the capacitance of the gap 124 created by the label 110 or the web 108. The pulse width modulated signal on line 104 is then fed to the processing module 106 for subsequent processing.

To isolate the sensing electrode 112 from noise sources such as surrounding areas of differing potentials, shielding electrode 114 is also driven to a similar potential with a resulting waveform of exactly the same frequency by a shield dedicated monostable multivibrator 132. The waveform is provided to the shielding electrode through electrical conductor 120.

To drive the shielding electrode 114 so that the mutual capacitance between the shielding electrode 114 and the sensor electrode 112 is minimized, the capacitance between the shielding electrode 114 and the ground electrode 116, as well as other stray capacitances experienced by the shield electrode 114, must be considered. Ideally, the recharging waveform of the shielding electrode 114 should replicate the recharging waveform of the sensor electrode 112 at all times.

To match the recharging waveforms, the time constants must be made equal and the recharge cycle for each must begin at precisely the same time. This synchronization is accomplished by feeding the shield dedicated monostable multivibrator 132 the same clock pulse 140 that is fed to the sensor dedicated monostable multivibrator 136. To match the time constants, the recharge resistor 134 connecting the dedicated multivibrator 132 and the shielding electrode 114 to the DC power supply (not shown) must be properly matched to the capacitance existing between the shielding electrode 114 and the ground electrode 116 and other undesired ground surfaces. Since $C_{Probe}$ 126 does not equal the capacitance experienced by the shield electrode 114 including $C_{shield}$ 128 and $C_{stray}$ 129, the resistance of the shield recharge resistor 134 will not be equal to the resistance of the sensor recharge resistor 138.

Figure 4:
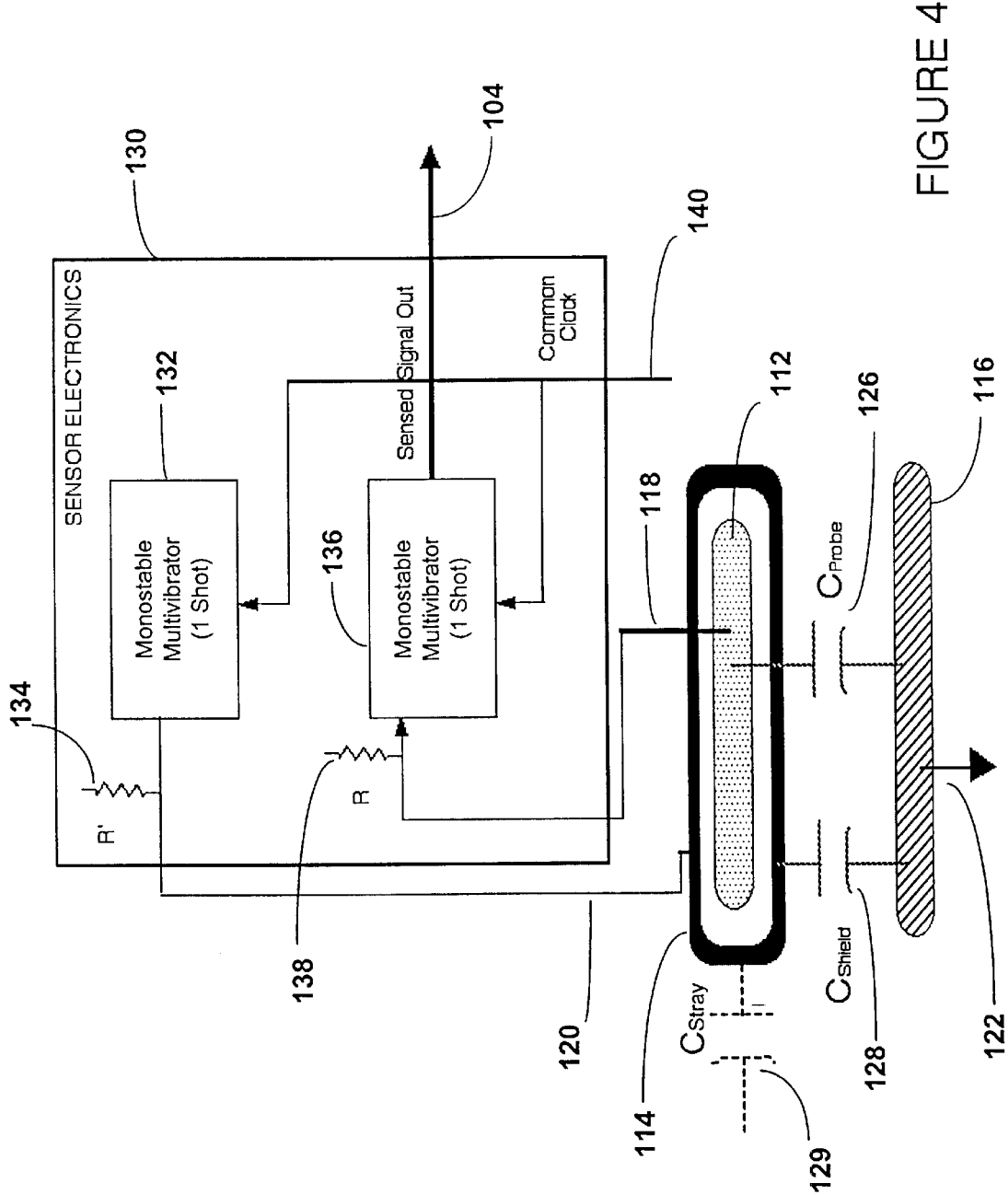
FIG. 4 illustrates the sensor unit's electronics.

The sensor electronics 130 of FIG. 4 permit the shield electrode 114 to be independently driven. The multivibrators 132 and 136 operate in unison to generate the independent signals and thereby prevent mutual capacitance from developing between the sensor and shield electrodes. This dual-multivibrator method not only creates very similar charging characteristics for both electrode capacitances, but also creates virtually identical fast-slewing discharge slopes, as well.

Figure 5:
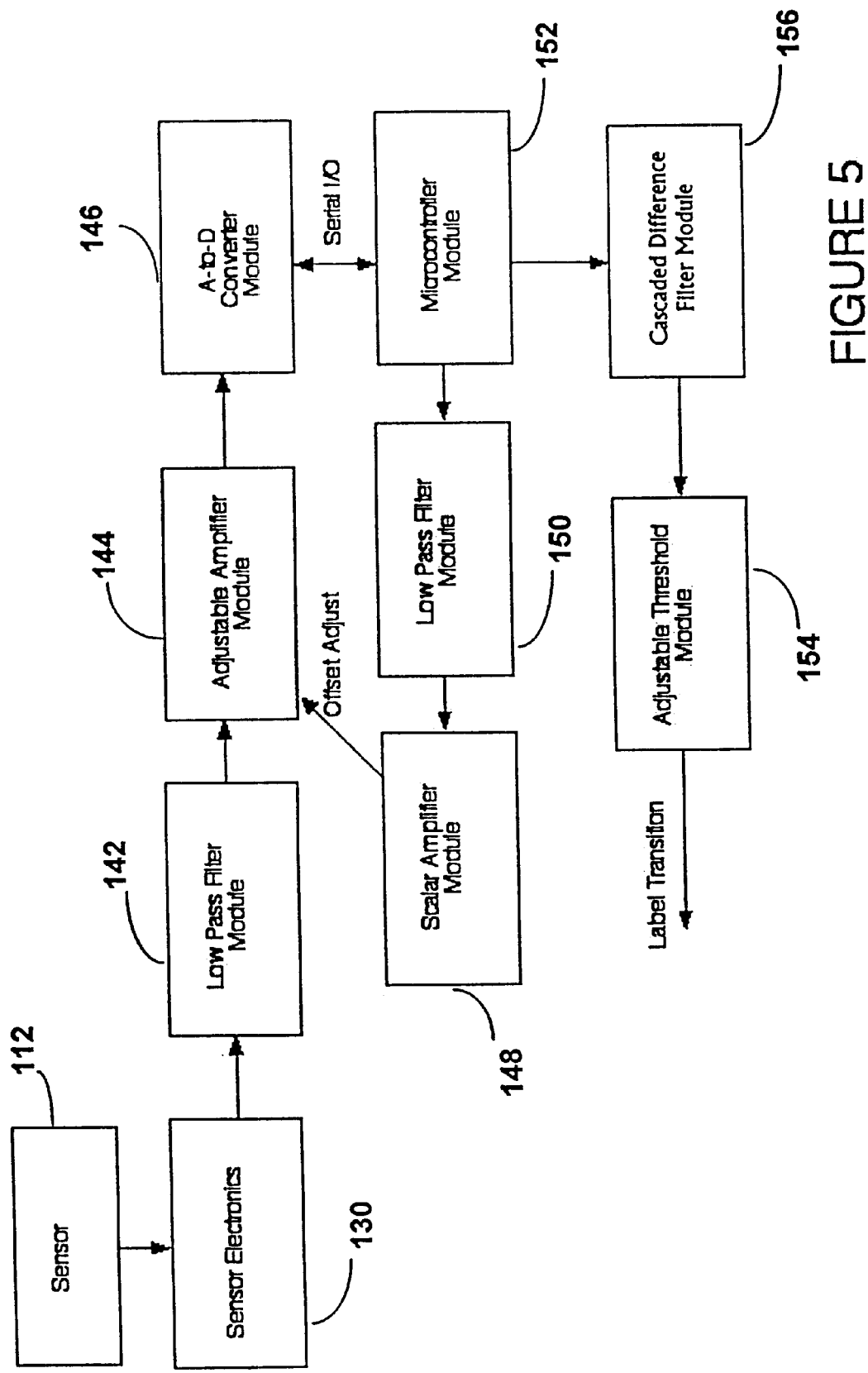
FIG. 5 is an electrical block diagram of the sensor unit and the processing module.

FIG. 5 illustrates the system electronics. The embodiments of the electronics of the invention described herein are implemented as logical operations in the detection system. The logical operations are implemented (1) as a sequence of computer implemented steps running on a computer system comprising the processing module and (2) as interconnected machine modules running within the computing system. This implementation is a matter of choice dependent on the performance requirements of the computing system implementing the invention. Accordingly, the logical operations making up the embodiments of the invention described herein are referred to as operations, steps, or modules. It will be recognized by one of ordinary skill in the art that these operations, steps, and modules may be implemented in software, in firmware, in special purpose digital logic, in analog circuits, and any combination thereof without deviating from the spirit and scope of the present invention as recited within the claims attached hereto. In the preferred embodiment, the modules described herein embody a microprocessor.

The sensor electrode 112 feeds its detection signal (i.e. the recharge signal) to the sensor electronics 130. The pulse width modulated periodic signal from the sensor electronics 130 travels to a low pass filter module 142 where it is then integrated into a varying DC analog output signal. The cutoff frequency of the low pass filter 142 is selected so that the high frequency content of the pulses is removed. The low frequency component which represents slow changes in the sensor capacitance passes through to create the varying DC signal.

The width of the pulse produced by the sensor electronics 130 varies depending upon the capacitance of the gap 124, which is governed by whether a label is present in the gap 124. If a label is present, the pulse width is greater than when only the web is present. The greater the pulse width, the greater the DC level of the signal output by the filter 142, which varies proportionally to the pulse width.

The varying DC signal travels to the adjustable amplifier module 144. This module 144 takes the DC signal and amplifies it to a greater level suitable for digitization. Ultimately, the system determines the presence of a label edge by determining whether the DC signal rises or falls. Amplifying the signal expands the rise or fall so that it is easily detected when digitized.

The amplified varying DC signal travels to an analog-to-digital (A/D) converter module 146 which samples the signal to produce a steady stream of discrete values indicating the amplitude of the varying DC signal at any sampling time. The discrete amplitude values are then output through a serial data bus into a microcontroller module 152.

The microcontroller module 152 receives the digitized stream of values representing the varying DC signal and then processes the signal to determine label edge transitions. The microcontroller 152 also automatically adjusts the offset voltage applied to the adjustable amplifier module 144 to compensate for voltage drift caused by changes in the ambient conditions, such as temperature and humidity, and changes in label stock. Additionally the microcontroller 152 automatically adjusts the threshold used to determine rising and falling signals to compensate for variation in overall signal levels caused by changes in label or web dielectric value. Therefore, the microcontroller 152 runs at least three processes contemporaneously, each of which is discussed herein. Alternatively, multiple microcontrollers could receive the digitized data to reduce the number of processes that must be performed by each one.

In one embodiment, the microcontroller 152 applies a cascaded difference filter module 156 to the digitized data to remove noise components so that the rise and fall of the varying DC signal is more easily detected. The operation of the cascaded difference filter will be discussed in greater detail below.

The microcontroller 152 automatically adjusts the threshold used by the cascaded difference filter 156 to determine the presence of a label edge by continuously analyzing the peak-to-peak amplitude of the varying DC signal. The automatic threshold adjustment function is performed by the adjustable threshold module 154. The operation of the adjustable threshold module 154 will also be discussed in greater detail below.

The microcontroller 152 also automatically adjusts the offset voltage that is applied to the adjustable amplifier module 144. The microcontroller 152 continuously analyzes the mean value of the varying DC signal to determine whether the offset is appropriate. The microcontroller 152 outputs a pulse width modulated signal whose pulse width varies depending upon the offset voltage error. If the microcontroller 152 determines that the adjustable amplifier 144 offset is either too high or too low, then it alters the width of the pulse that it generates. If the offset is too high, the pulse width is increased, and if the offset is too low the pulse width is decreased.

The PWM signal generated by the microcontroller 152 travels to another low pass filter module 150. The low pass filter 150 integrates the fixed frequency PWM signal down to a DC offset correction voltage. This low pass filter 150 has a cutoff frequency that is set so that the high-frequency content of the PWM signal is removed. Therefore, a 0% duty cycle signal (no pulse) results in a ground level DC offset correction voltage output, and a 100% duty cycle signal (full width pulse) results in a maximum level DC offset correction voltage output.

The DC offset correction voltage created by the low pass filter 150 is fed to a scalar amplifier module 148 that amplifies the DC offset correction voltage to an amount suitable to correct the offset voltage error of the adjustable amplifier 144. The adjustable amplifier 144 receives the amplified DC offset correction voltage and adds it to the varying DC signal before it is output to the A/D converter 146. The offset adjustment process is discussed in greater detail below. The low pass filter 150 and scalar amplifier 148 and microcontroller 152 operate together to form an offset adjusting module.

Figure 6:
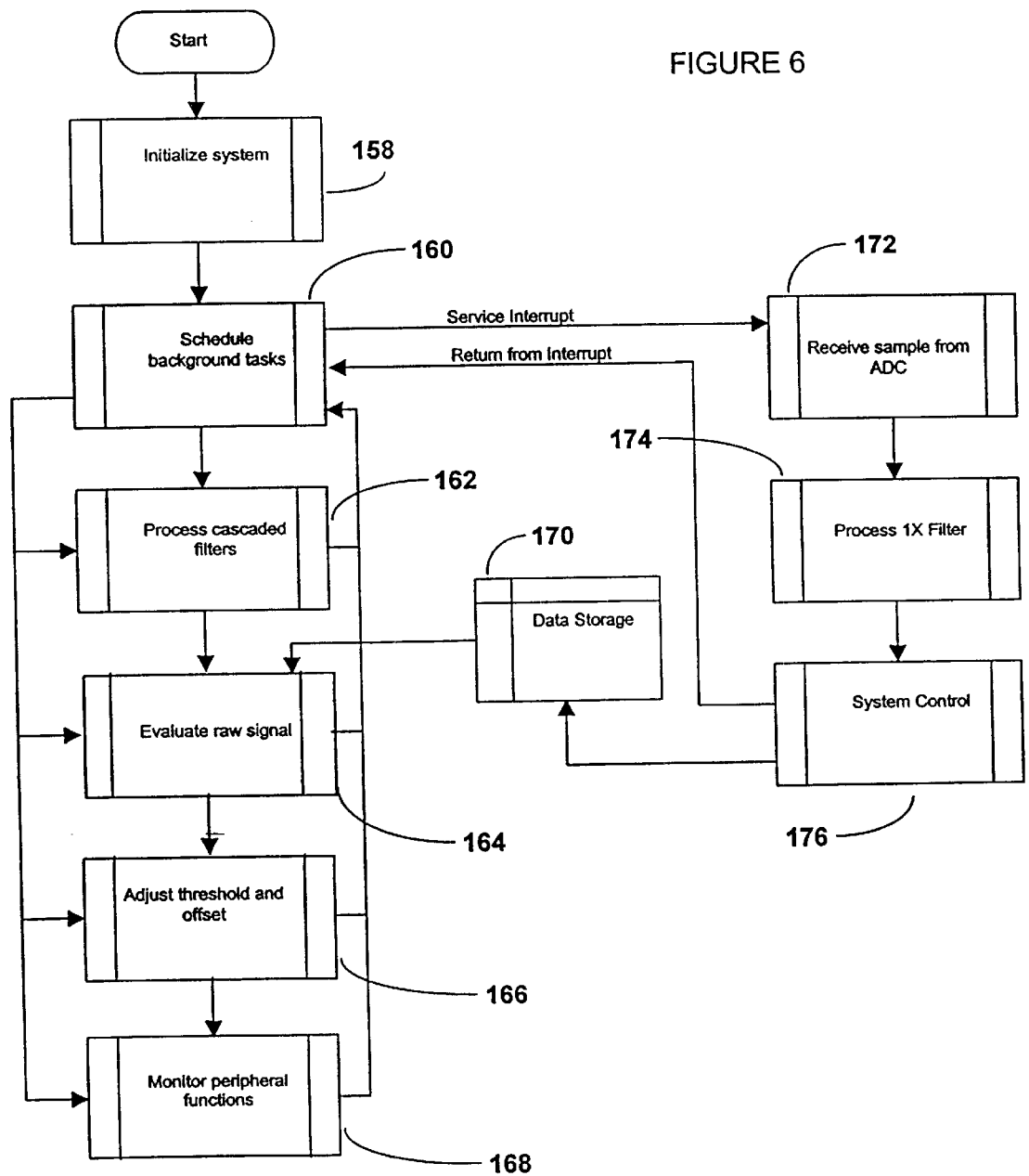
FIG. 6 illustrates the operational flow for the data acquisition and automatic adjustment processes.

FIG. 6 illustrates the operational flow of the data acquisition and background routines performed by the microcontroller 152. At operation 158, the system becomes initialized so that it is ready to begin receiving, processing, and storing data from the A/D converter. Operation 160 includes scheduling background tasks so that once data is received, the microcontroller 152 can begin to automatically adjust the threshold and offset and apply the cascaded difference filters. Once these tasks are scheduled, a service interrupt is provided to operation 172 which begins to receive data samples from the A/D converter.

Process operation 174 then applies a 1× (every sample) difference filter, discussed below, to remove the DC component from the data, and look for signal transitions. Once the difference filter has generated output, control operation 176 feeds the output into storage at store operation 170. Control operation 176 sends a return from interrupt back to schedule operation 160. The background routine begins once the return from interrupt signal is received.

During the background routine, process operation 162 applies the cascaded difference filters to the data being provided by the A/D converter. The cascaded difference filters look for signal transitions and generate a digital pulse whose rising and falling transitions correspond to the presence of leading and trailing label edges.

The background routine also involves evaluate operation 164 which receives the raw signal data that has been filtered and stored. This operation analyzes the data to determine several specific values that are subsequently used to adjust the threshold and offset voltages in operation 166. During the background routine, monitor operation 168 continuously oversees the processing, evaluation, and adjustment tasks and flags the schedule operation 160 when a problem occurs.

Figure 7A:
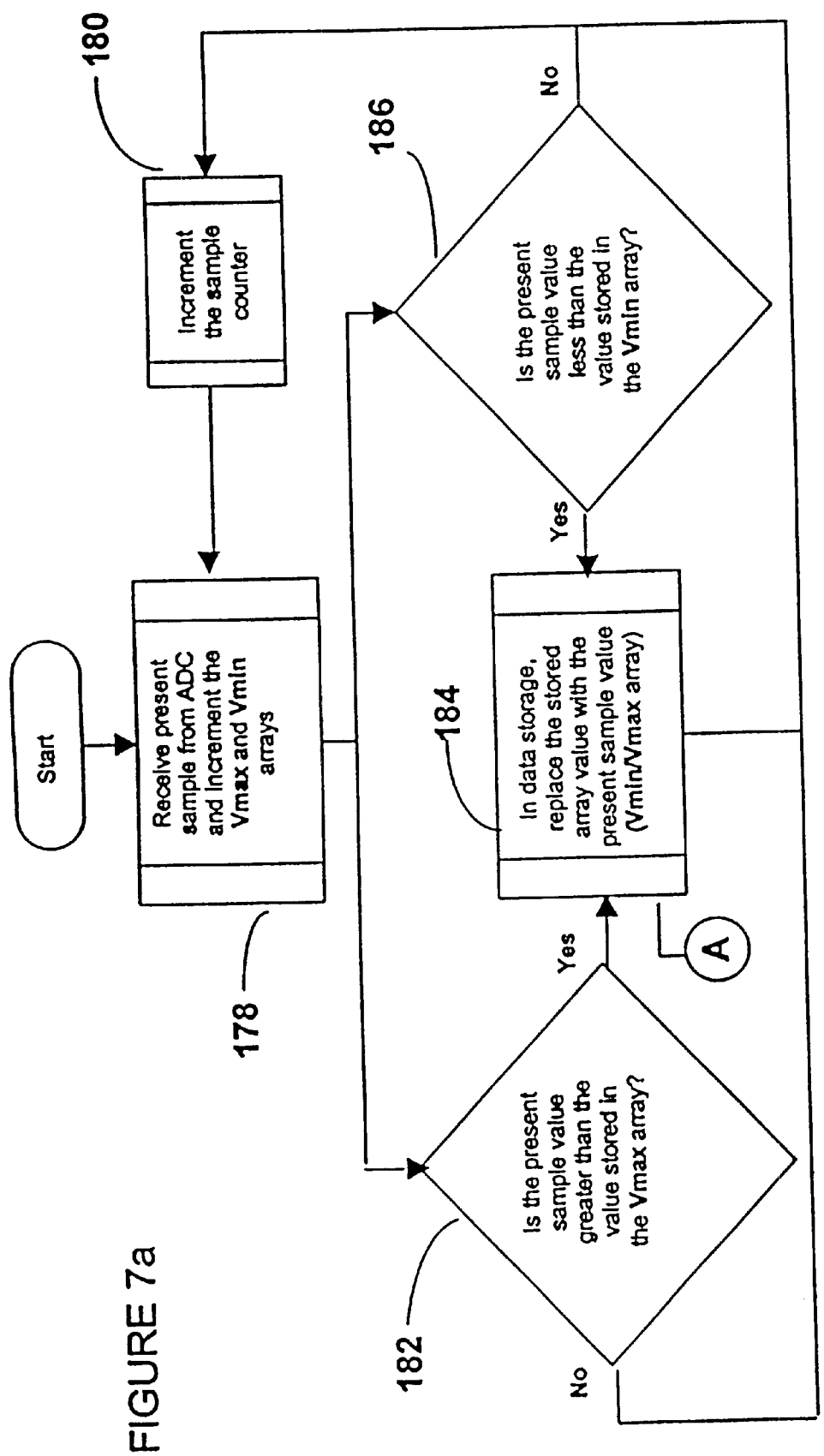
FIG. 7a shows the operational flow of the data acquisition process in greater detail.

FIG. 7a depicts the signal sampling, data accumulation, and raw data evaluation routine in more detail. This routine derives the data that is used to determine the raw signal's amplitude and its relative position between ground and the amplifiers voltage rail. Receive operation 178 begins to accept data through the serial I/O bus from the A/D converter and stores the digitized voltage levels in data arrays. One data array (Vmax) contains the highest signal levels detected by operation 182 since the beginning of an adjustment interval and another array (Vmin) contains the lowest signal levels detected by operation 186 since the beginning of an adjustment interval.

Query operation 182 detects whether the present sample is greater than the value stored in the Vmax array. If so, the value stored in the Vmax array is replaced with the current value at replace operation 184. Then increment operation 180 increases the sample counter by 1. The sample counter tracks the number of samples processed during a given adjustment interval. If the current value is not greater than the Vmax value, then control moves directly to increment operation 180.

Figure 7B:
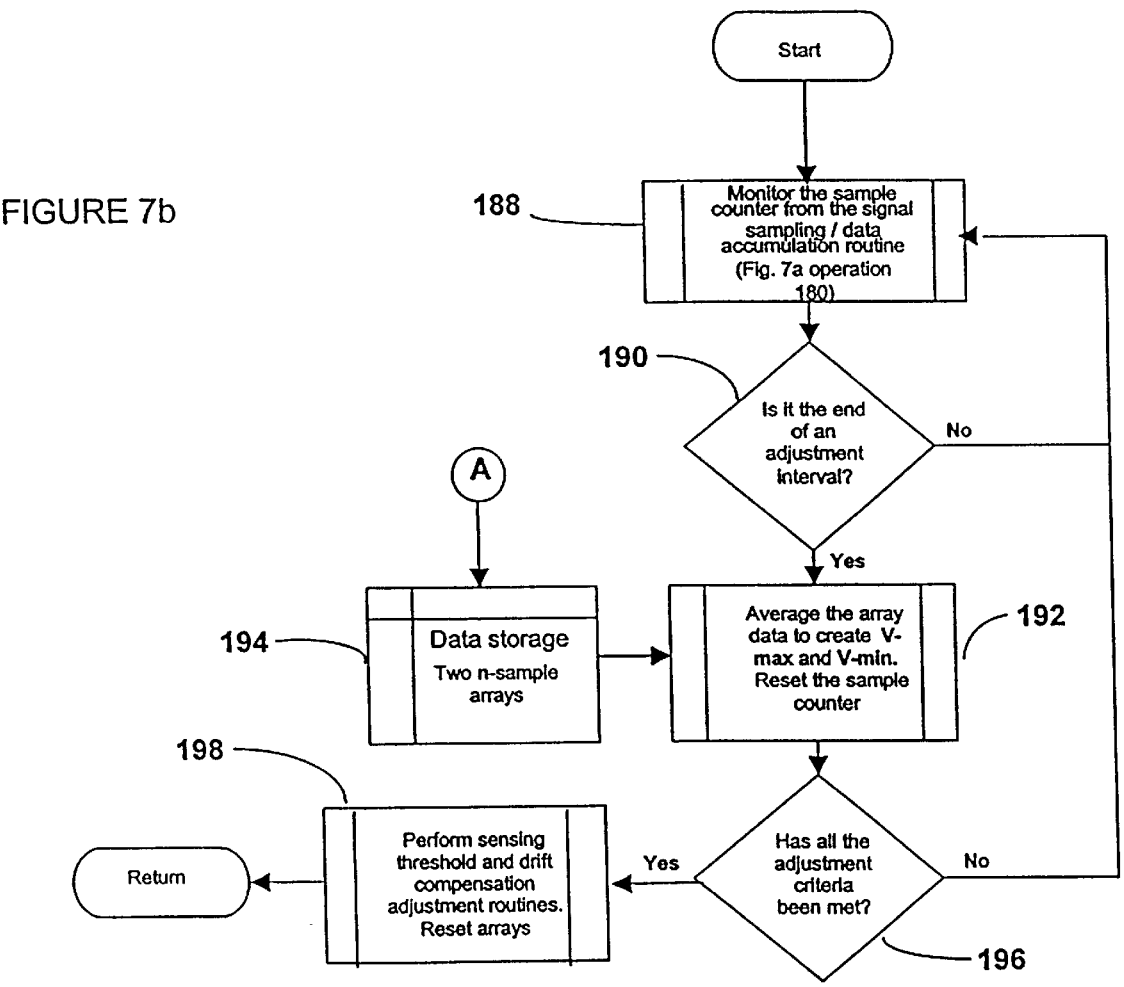
FIG. 7b depicts the operational flow of the automatic adjustment process in greater detail.

Query operation 186 detects whether the present sample is less than the value stored in the Vmin array. If so, the value stored in the Vmin array is replaced with the current value at replace operation 184. This query operation occurs in parallel with query operation 182 so that control moves from either query operation to increment operation 180 at the same time. Also, once these query operations and replace operation 184 are finished, the data received is stored at storage operation 194 of FIG. 7b.

The Vmax and Vmin arrays accumulate the highest and lowest signals sampled during the adjustment interval. At the end of each interval, which is detected by operation 188 monitoring the sample counter and query operation 190 determining that the sample counter has reached its target, the data stored at operation 194 in the Vmax array is averaged at operation 192, as is the data stored in the Vmin array, to produce an average Vmax and an average Vmin. These values are used in both the automatic threshold and automatic offset voltage adjustments.

Query operation 196 detects whether all of the adjustment criteria has been met, which includes determining that average values for both Vmax and Vmin are known. If they are not known, the control returns to monitor operation 188 which looks for the end of the next adjustment interval. If they are known, then control moves to perform operation 198 where both the threshold and offset routines are then performed and the arrays are reset. The process then repeats which allows the sensor to continually optimize the threshold and offset settings based on data from the previous adjustment interval.

Figure 8:
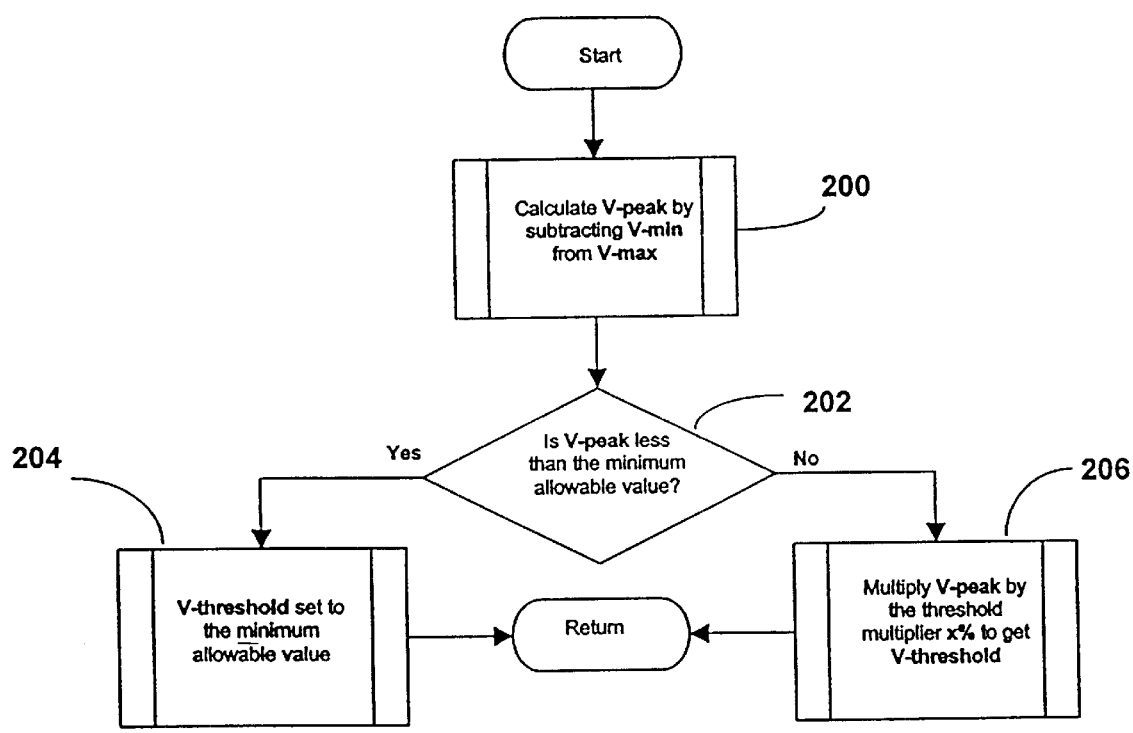
FIG. 8 illustrates the operational flow of the automatic threshold adjustment process.

The process for automatically adjusting the threshold value used to detect a rising or falling transition is depicted in FIG. 8. This threshold adjustment routine sets the threshold at a desired percentage of the peak-to-peak raw signal amplitude to optimize the threshold for the raw signal level. This method maintains a high degree of noise immunity over a wide range of input signal amplitudes.

At calculate operation 200, the peak-to-peak raw signal amplitude (Vpeak) is found by subtracting the average Vmin value previously determined from the average Vmax value that was also previously determined. Once Vpeak is known, query operation 202 detects whether Vpeak is less than the minimum allowable value. This operation is necessary because the threshold voltage must remain at least above a minimum level regardless of the Vpeak to avoid noise interference. If query operation 202 detects that Vpeak is below a minimum value, adjust operation 204 sets the threshold voltage to its minimum value.

If query operation 202 detects that Vpeak is above or equal to its minimum value, flow moves to adjust operation 206. Here, the threshold voltage is obtained by multiplying Vpeak, the peak-to-peak raw signal amplitude, by the desired percentage to produce the appropriate threshold. The threshold voltage has no upper limit other than the limit indirectly imposed by the potential difference between ground and the voltage rail of the amplifier module 144. After the threshold voltage is adjusted, operational flow returns to await the calculation of the next average Vmin and Vmax values. The system continuously optimizes the threshold voltage for variances in the raw signal amplitude in this manner.

Figure 9:
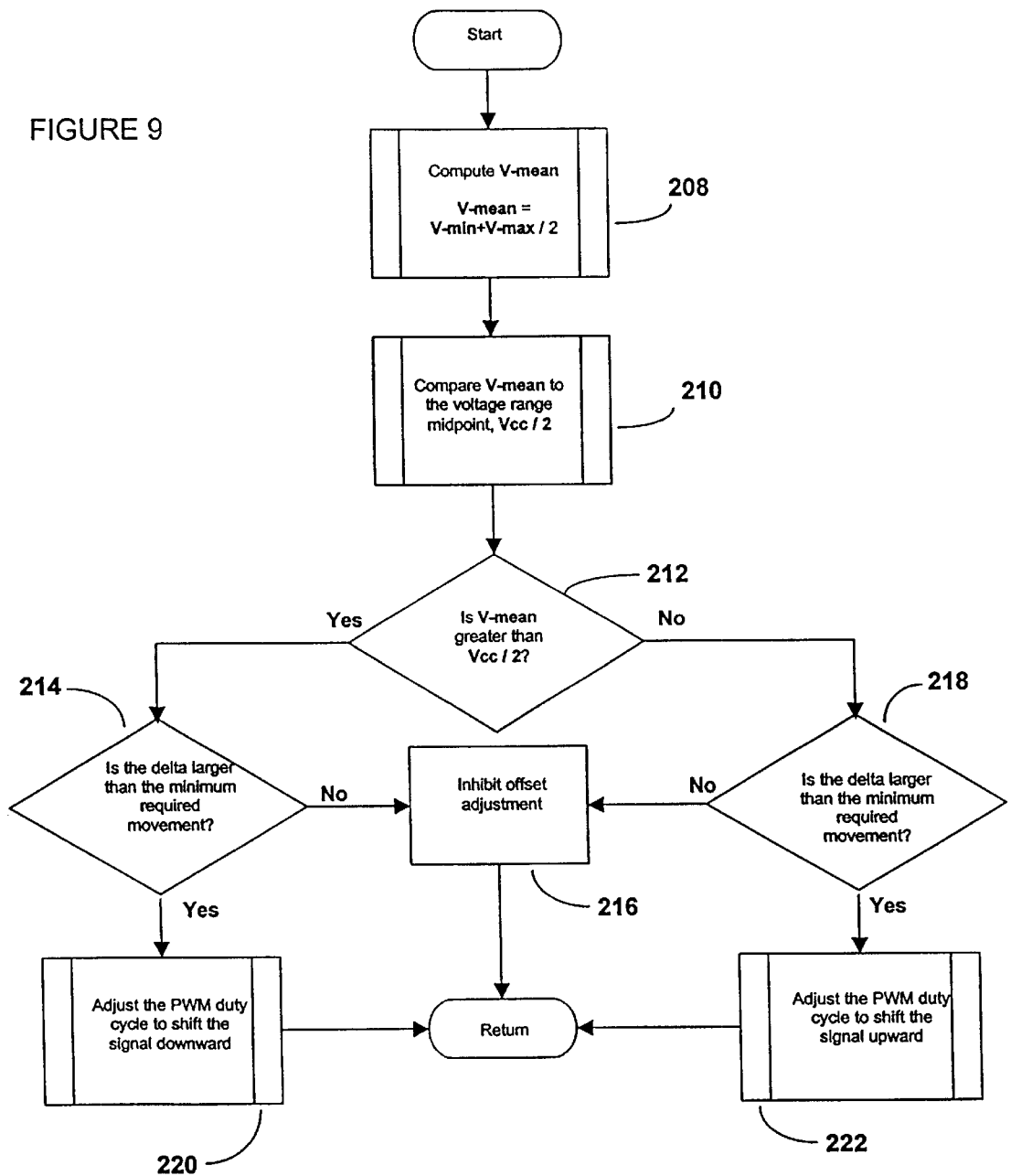
FIG. 9 shows the operational flow of the automatic offset adjustment process.

FIG. 9 shows the operation flow of the automatic offset, or drift compensation routine. This routine permits the system to maintain the mean signal level Vmean centered between the voltage rail of the amplifier module 144 and ground. Centering Vmean in this way allows maximum signal compliance and measuring accuracy. This routine compensates for amplifier output voltage drift that occurs as a result of changes in the ambient conditions including humidity and temperature, or the dielectric constant of the label which may change from web to web.

Calculate operation 208 begins the routine by computing Vmean. The average Vmin previously determined is added to the average Vmax also previously determined. This sum is divided by two to find Vmean. Compare operation 210 subtracts the Vmean value from the amplifiers voltage rail value divided by two. Query operation 212 detects whether Vmean is greater than the voltage rail divided by two. If so, then flow moves to query operation 214 to test whether the difference between Vmean and the voltage rail divided by two is larger than a chosen minimum adjustment value.

If the difference is not larger than the chosen minimum, then no offset adjustment is required because Vmean is sufficiently centered between the voltage rail of amplifier module 144 and ground. Therefore, inhibit operation 216 maintains the PWM duty cycle and the routine returns to the beginning where it awaits the next Vmin and Vmax. If query operation 214 detects that the difference is larger than the chosen minimum, then adjust operation 220 increases the duty cycle of the PWM signal being sent to the low pass filter 150 which results in an offset adjustment that lowers Vmin and Vmax when an inverting amplifier 144 is used to magnify the signal. A non-inverting amplifier 144 could be used as well, in which case the duty cycle of the PWM waveform would be decreased to decrease Vmin and Vmax. The offset amount applied is the amount necessary to make (Vmin+Vmax)/2=Vcc (voltage rail)/2.

If query operation 212 detects that Vmean is not greater than Vcc/2, then query operation 218 tests whether the difference is larger than the chosen minimum required. If the difference is not larger, then Vmean is sufficiently centered and inhibit operation 216 maintains the PWM duty cycle and the routine returns to the beginning where it awaits the next Vmin and Vmax. If the difference is larger, then adjust operation 222 decreases the duty cycle of the PWM waveform that results in an increase in Vmin and Vmax when the amplifier 144 is inverting. Again, a non-inverting amplifier 144 could be used as well, in which case the duty cycle of the PWM waveform would be increased to increase Vmin and Vmax. The offset amount applied is again the amount necessary to make (Vmin+Vmax)/2=Vcc/2.

Figure 10:
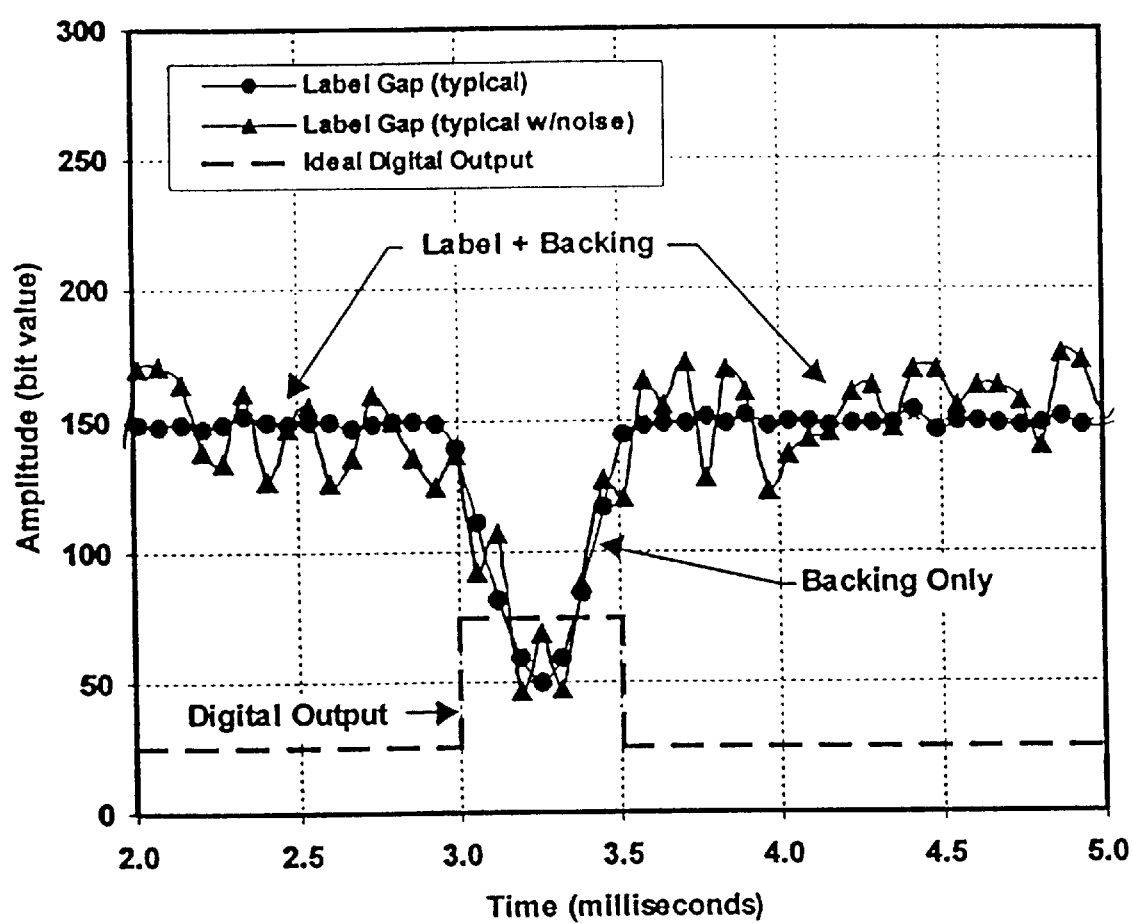
FIG. 10 shows the label detection signal with and without noise and also shows the ideal digital output signal that results.

FIG. 10 illustrates a typical waveform that results from a label to web to label transition. The line with the round data point markers shows a typical waveform in the presence of virtually no background noise. As can be seen, the signal level is high when the capacitance is high due to the presence of both the label and its supporting web. When the label moves out of the gap 124 so that only the web is present, the capacitance decreases and the signal level falls. Then, a new label enters the gap 124 and the signal level rises back to a high state.

The waveform with triangular data points depicts the signal when background noise is present, and the dashed line shows the ideal digital output produced by the processing module in response to the digitized input waveform. The ideal digital output indicates that the pulse goes high when the signal falls below the threshold and the pulse returns to the low state when the signal rises above the threshold. The system may be configured so that the falling signal threshold and the rising signal threshold are not equal. Also, it should be noted that the time frame of the label to web to label transition, depicted as 0.5 milliseconds, can vary greatly in operation. Typically, start up and shut down cycles, where the web is accelerating from rest or decelerating to rest, can cause label transition durations to vary from normal operating speed durations by a factor of 1000.

Detecting both the leading and trailing edges of the waveforms is desirable. Analog components can detect these edges but due to the variance in operating speed from rest to normal, it requires a system that can differentiate the transitions from near DC to high frequencies. Analog components cannot easily differentiate across such a broad bandwidth and are also very sensitive to ambient conditions. Therefore, digital filters are preferred in finding the transitions.

One technique for locating transitions in a signal is to quantify the change in the signal from sample to sample by subtracting adjacent data values. This subtraction (or difference) can be implemented through a digital finite impulse response filter. The basic equation describing this filter is $$y(t) = \sum_{n=0}^{n=(N-1)} h(n) \cdot x(t-n)$$

Figure 11:
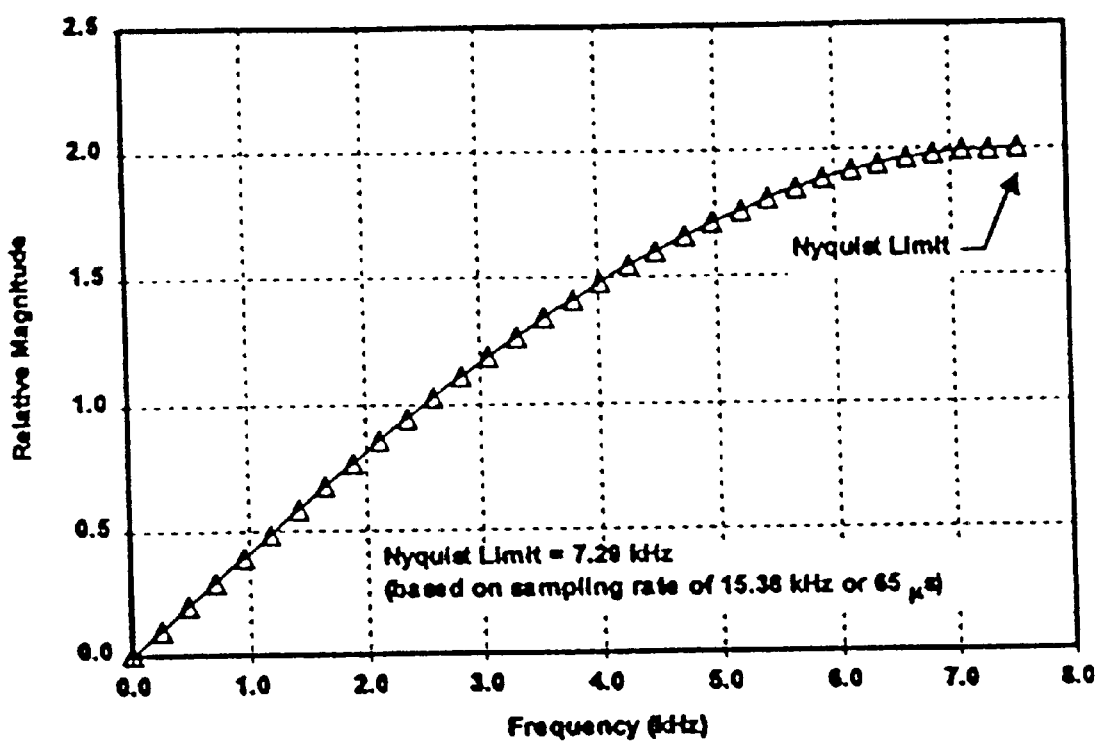
FIG. 11 illustrates the frequency passband characteristics for a 1× difference filter.

In this equation, x(t) represents the input waveform and y(t) represents the output waveform that has been filtered. N represents the total number of filter coefficients to be convolved with the input waveform. The filter coefficients are h(n). The filter coefficients corresponding to subtracting adjacent data values (to be referred to as a "1×" difference filter) are shown in Table 1 and the resulting amplitude values are shown in the passband plot of FIG. 11 (assuming a 65 microsecond sampling interval).

TABLE 1

| 1× Differencing Filter Coefficients | |
| --- | --- |
| Array number (n) | 1× difference filter coefficients h(n) |
| 0 | 1 |
| 1 | −1 |

The 1× difference filter is a fast filter because it accounts for every data sample point in the signal. As can be seen, the frequency plot of this filter slopes positively with increasing frequency from zero to the Nyquist sampling limit that equals one half of the sampling frequency. At DC, the passband amplitude is zero, and the passband amplitude peaks at the Nyquist limit.

Figure 12:
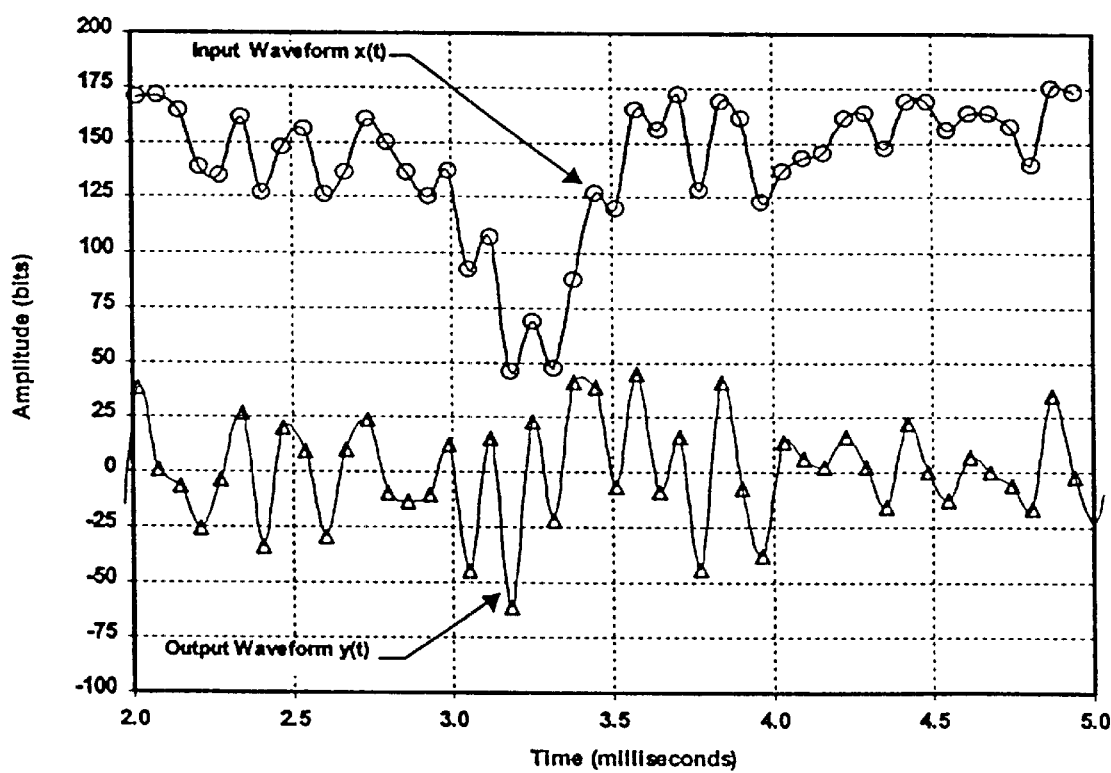
FIG. 12 depicts the input waveform of a label sensor and the resulting output waveform after application of the 1× difference filter.

FIG. 12 shows the input waveform for a label to web to label transition with background noise present. Also shown in FIG. 12 is the output of the 1× difference filter applied to the input waveform. The DC component is removed by the filter but the transitions cannot be resolved because the filter is too fast. To slow down the filter, the interval between samples considered by the filter are lengthened by only looking at data points spaced farther apart. For example, instead of taking the difference between every data point, the difference between every fourth data point can be taken instead. This filter is known as a 4× filter. Its coefficients are shown in Table 2.

TABLE 2

| 4× Difference Filter Coefficients | |
| --- | --- |
| Array number (n) | 4× difference filter coefficients h(n) |
| 0 | 1 |
| 1 | 0 |
| 2 | 0 |
| 3 | 0 |
| 4 | −1 |
| 5 | 0 |
| 6 | 0 |
| 7 | 0 |

Figure 13:
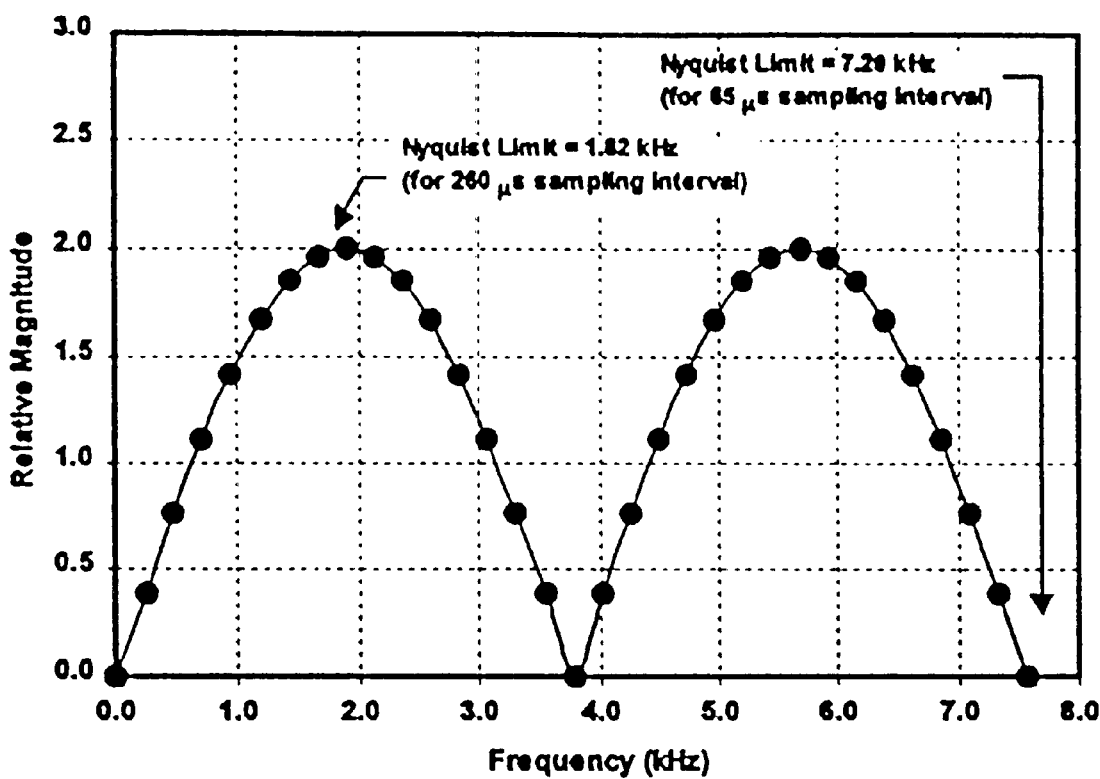
FIG. 13 depicts the frequency passband characteristics for a 4× difference filter.
Figure 14:
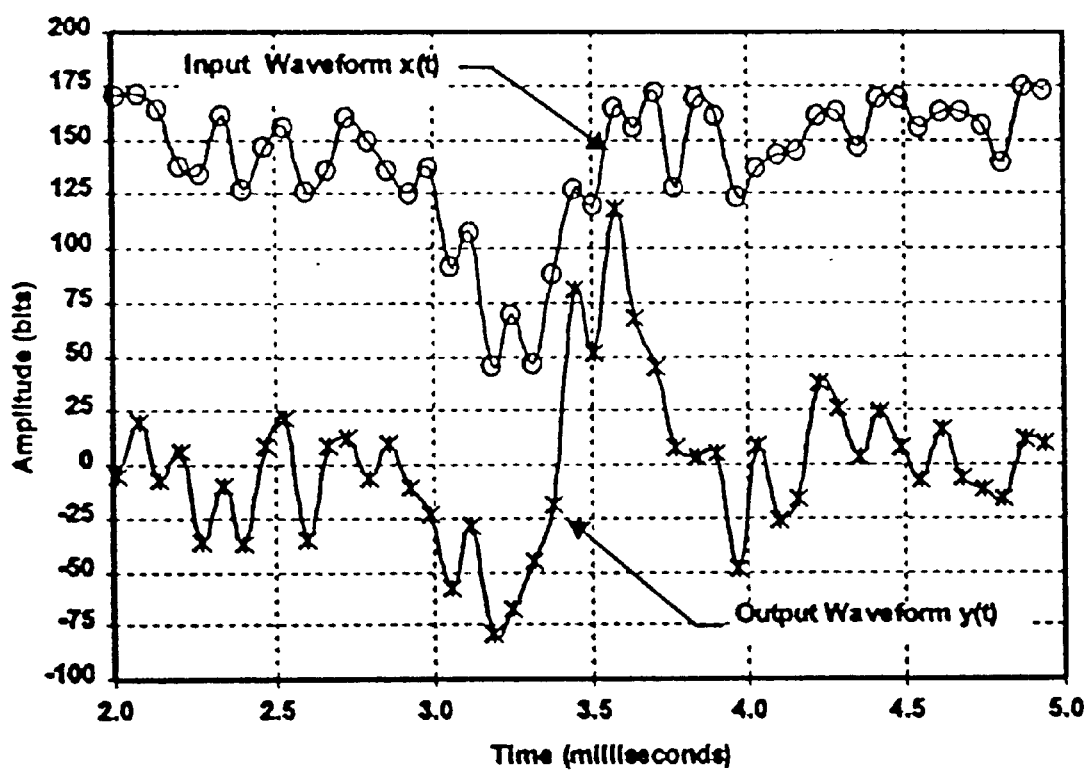
FIG. 14 shows the input waveform of a label sensor and the resulting output waveform after application of the 4× difference filter.

The frequency characteristics for the 4× filter (assuming a 65 microsecond sampling interval) are shown in FIG. 13. As can be seen, the 4× filter provides two passbands from DC to the Nyquist limit. The effect of the 4× filter on the input waveform can be seen in FIG. 14. the rise and fall transitions are now more apparent. However, high frequency noise remains in the output signal. Ordinarily, the bandwidth of the input signal for the 4× filter should be limited to one-fourth of the Nyquist limit to prevent high frequency from discoloring the output. The input waveform corresponding to the output waveform of FIG. 14 was bandwidth limited by the 1× filter, which only requires that the bandwidth be limited to the Nyquist limit (with the Nyquist limit being defined as the sampling interval of the 1× differencing filter or the rate at which the input waveform is being sampled).

To limit the bandwidth for the 4× filter, the input coefficients can be modified to cause the filter to also act as a low pass filter. Adjusting the filter so that a running average of the original waveform is performed before the subtractions are made will establish the low pass effect. This running average can be done by making the coefficients equal to one-fourth of the value used when no averaging is performed. The averaging coefficients are shown in table 3.

TABLE 3

4× Differencing Filter Coefficients (with averaging)

| Array number (n) | 4× difference filter coefficients h(n) |
|---|---|
| 0 | 0.25 |
| 1 | 0.25 |
| 2 | 0.25 |
| 3 | 0.25 |
| 4 | −0.25 |
| 5 | −0.25 |
| 6 | −0.25 |
| 7 | −0.25 |

Figure 15:
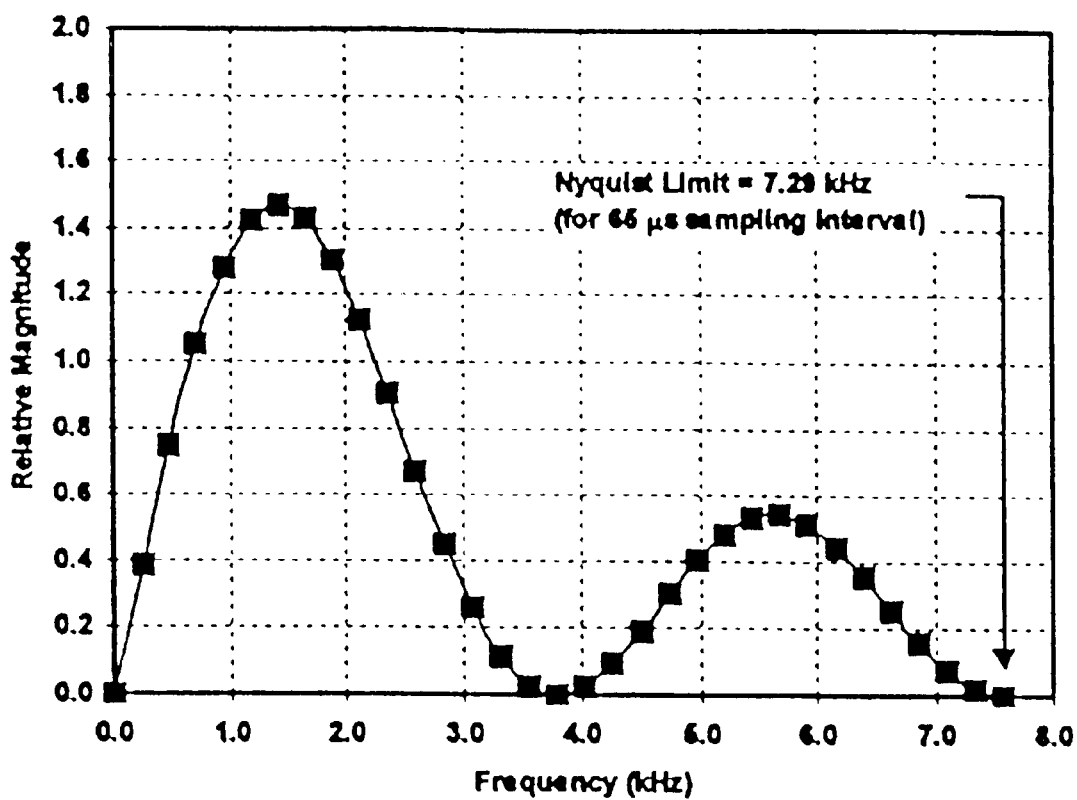
FIG. 15 illustrates the frequency passband characteristics of a 4× difference filter using averaging.

The passband characteristics of the 4× filter with averaging can be seen in FIG. 15. The two passbands are still provide up to the Nyquist limit but both passbands' amplitudes are reduced. The higher frequency passband's amplitude is greatly reduced relative to the lower frequency passband's amplitude.

Figure 16:
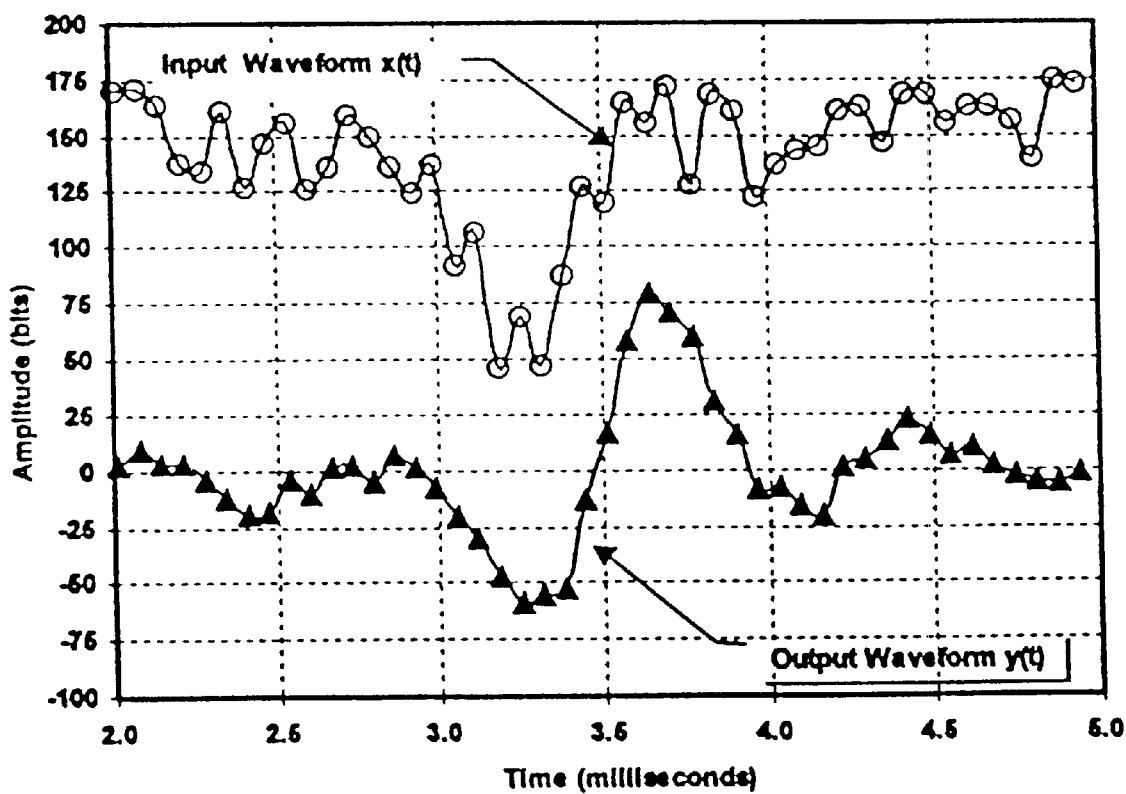
FIG. 16 depicts the input waveform of a label sensor and the resulting output waveform after application of the 4× difference filter using averaging.

FIG. 16 shows the input waveform output by the 4× difference filter using averaging. The transition thresholds are still apparent and the high frequency noise is greatly attenuated. The high frequency noise's amplitude is well below the level necessary to trigger a false label edge detection.

Implementing this average technique digitally is difficult because the input waveform's data points must be buffered over a long period of time. To minimize the amount of data that must be buffered while averaging, the system can be configured to compute a cumulative average rather than a running average. A running average is one that is updated with each new data point. A cumulative average is one that combines successive data point into a single value. Rather than storing each data point's value, the average for every four consecutive data points can be stored for comparison to the average of the next four consecutive data points for example. The output waveform produced by the filter using cumulative averaging will be every fourth data point of the output waveform produced by using running averaging.

Figure 17:
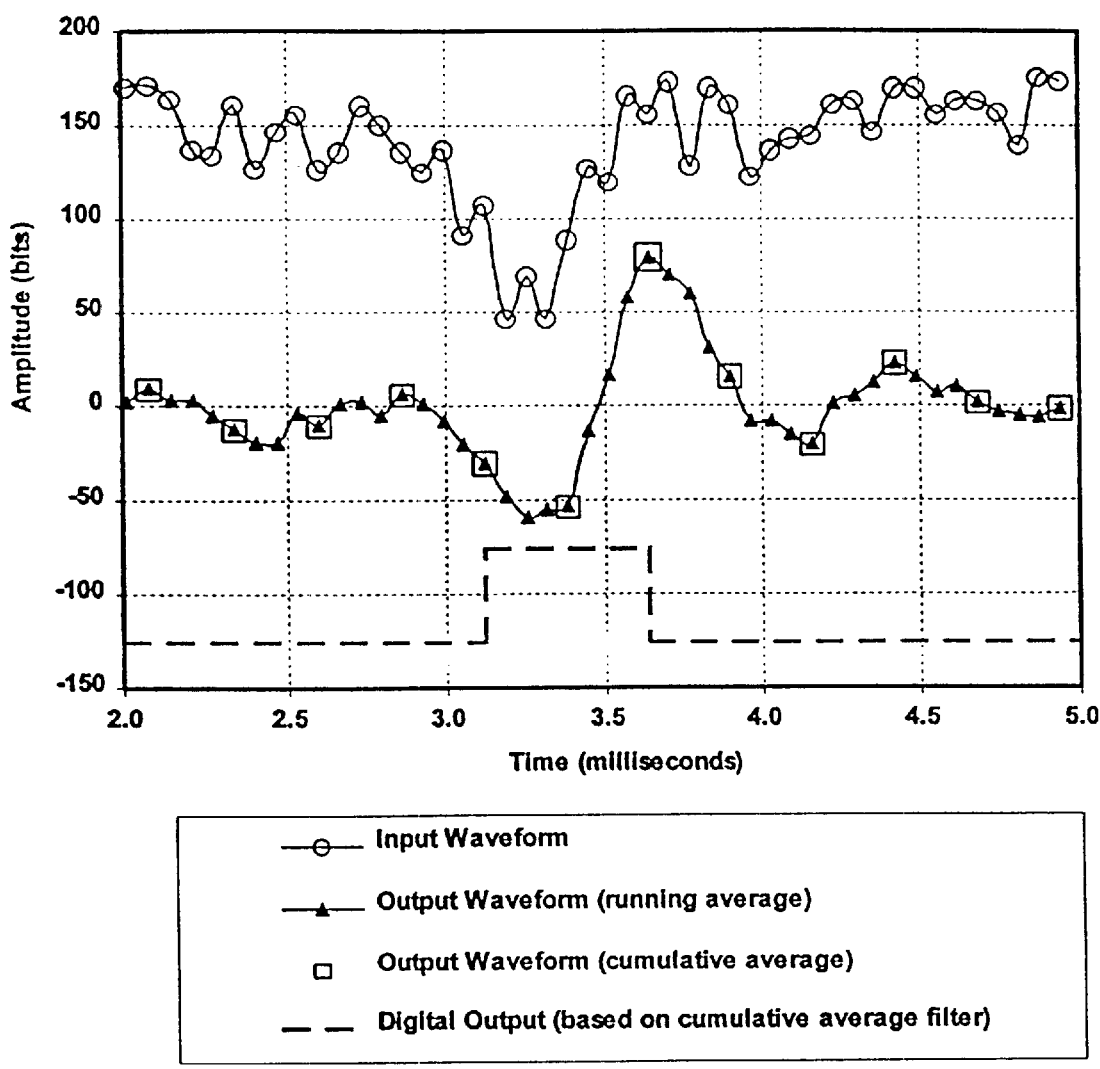
FIG. 17 depicts the input waveform of a label sensor, the output waveform as a running average, the output waveform as a cumulative average, and the digital output based on the cumulative average output.

FIG. 17 illustrates the input waveform, the running average output waveform, the cumulative average output waveform, and the digital output waveform based on the cumulative average filter. The cumulative average waveform contains one-fourth as many data points as the running average waveform but still provides sufficient granularity to detect the rise and fall transition thresholds. The digital output is triggered high when the fifth cumulative averaging data point's amplitude is below the falling threshold. The digital output is triggered back to low when the seventh cumulative averaging data point's amplitude is above the rising threshold.

Employing the cumulative averaging technique allows the system to implement the digital filter more quickly while requiring less memory usage. These two effects permit numerous difference filters of varying "speeds" to be cascaded. Using numerous filters provides the maximum bandwidth for evaluating the signals, and start up and shut down accelerations and decelerations on the web do not cause the label edges to become undetectable. Cascading the filters can also prevent false detections due to aliasing.

Figure 18:
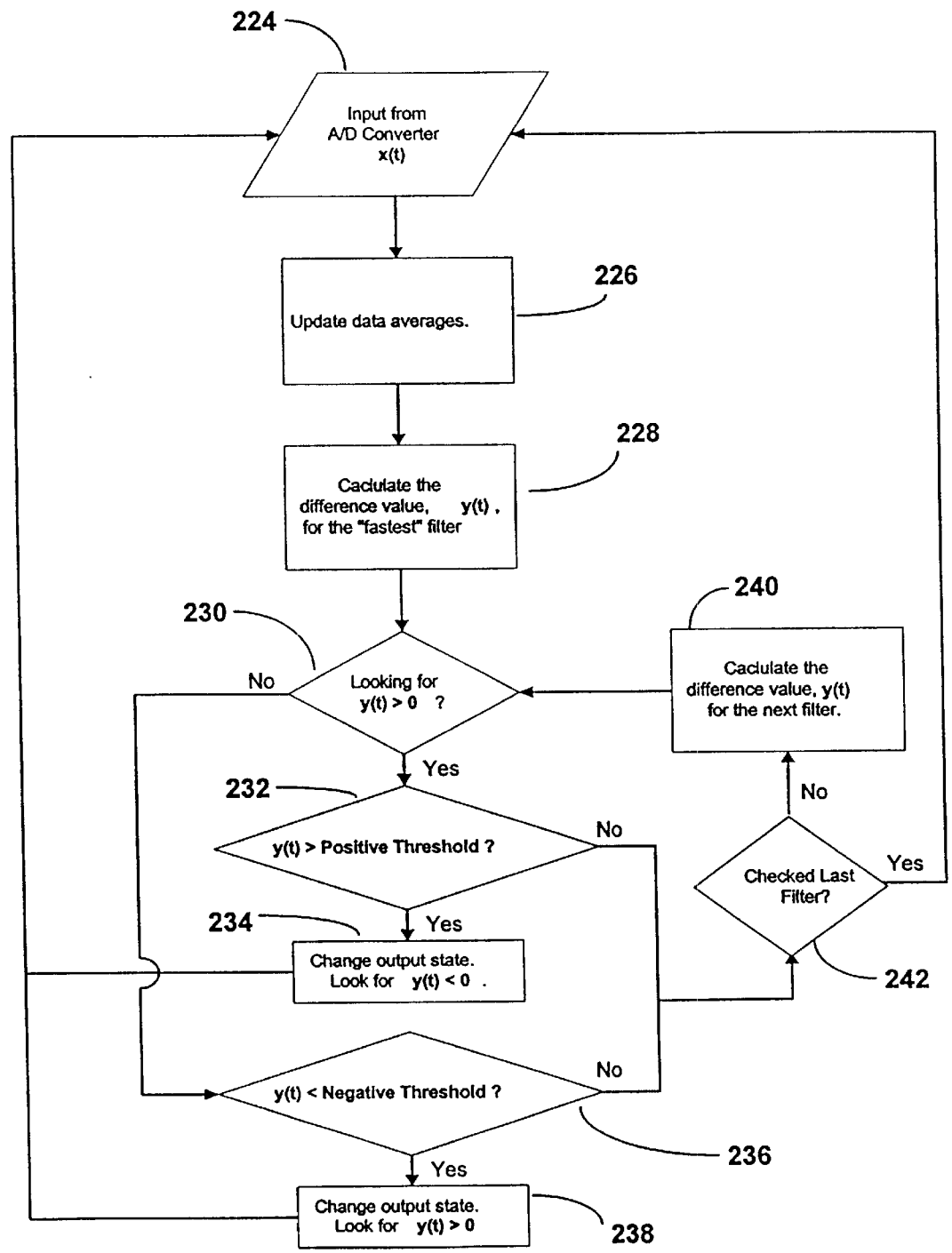
FIG. 18 shows the operational flow of a cascaded difference filter.

FIG. 18 illustrates the operational flow for the cascaded difference filter architecture and routine. At input operation 224, the filter receives input data x(t) from the A/D converter. The analog bandwidth limit of the A/D input signal x(t) is specified by the sampling interval for acquiring data from the A/D converter.

Once data is received, update operation 226 updates the average output value for each of the time intervals under consideration. Difference operation 228 calculates the difference value y(t), as previously described, for the fastest filter being used. Query operation 230 evaluates whether a positive or negative transition is currently required to change the output state. If looking for a positive transition, then query operation 232 tests whether y(t) is greater than the positive or rising threshold.

If y(t) is greater than the positive threshold, then state operation 234 changes the output state of the system to indicate a leading edge transition. Then control returns to input operation 224. If y(t) is not greater than the positive threshold, then query operation 242 detects whether the last filter has been checked. If so, then control returns to input operation 224. If not, the filter operation 240 calculates y(t) as previously described for the next fastest filter, and then control returns to query operation 230.

Back at query operation 230 for the first pass, if looking for a negative going transition (y(t)<0), then flow moves to query operation 236 to test whether y(t) is less than the negative or falling threshold. If it is, then state operation 238 changes the output state of the system to indicate a trailing edge transition, and control returns to input operation 224. If y(t) is not less than the negative threshold, then flow moves to query operation 242 to determine whether the last filter has been checked. If so, control returns to input operation 224. If not, control moves to filter operation 240 which calculates y(t) for the next fastest filter. Then control returns to query operation 230.

While the invention has been particularly shown and described with reference to preferred embodiments thereof, it will be understood by those skilled in the art that various other changes in the form and details may be made therein without departing from the spirit and scope of the invention.

We claim:

1. A method for providing a capacitive label sensor having a reference electrode coupled to a first side of an opening in the sensor, a sensor electrode coupled to a second side of the opening such that an object passes between the reference electrode and the sensor electrode, and a shield electrode coupled to the second side of the opening, the shield electrode surrounds the sensor electrode on the plane of the second side of the opening as well as on the side opposite the reference electrode, the method comprising:

electrically connecting the reference electrode to a system ground;

electrically connecting the sensor electrode to a first end of a first resistor and a first electronic driving circuit at a first connection, the first resistor is electrically coupled between the first connection and a supply voltage;

electrically connecting the shield electrode to a first end of a second resistor and a second electronic driving circuit at a second connection, the second resistor is electrically coupled between the second connection and the supply voltage; and determining the edge of the object passing through the opening of the sensor by determining a change in capacitance between the reference electrode and the sensor electrode.

2. The method according to claim 1, wherein the first electronic driving circuit is a first monostable multivibrator circuit having a clock signal input and generating an output signal.

3. The method according to claim 2, wherein the second electronic driving circuit is a second monostable multivibrator circuit having a clock signal input.

4. The method according to claim 3, wherein the first and second monostable multivibrator circuit clock signal inputs are electrically coupled to a system clock signal.

5. The method according to claim 4, wherein the system clock signal is a 2 MHz clock.

6. The method according to claim 2, wherein the method further comprises:

filtering the output signal using a low-pass filter to generate a capacitance signal; and determining a change in capacitance between the reference electrode and the sensor electrode by determining a change in the capacitance signal greater than a threshold value.

7. The method according to claim 1, wherein a first RC time constant is created by the first resistor and a first capacitance between the reference electrode and the sensor electrode, and wherein a second RC time constant is created by the second resistor and a second capacitance between the reference electrode and the shield electrode, the method further comprising:

matching the second RC time constant with the first RC time constant to minimize a mutual capacitance between the sensor electrode and the shield electrode.

8. An apparatus for providing a capacitive label sensor for determining an edge of a label located on a label web, the sensor having an opening to permit a label and label web to pass within the opening, the opening having first and second sides on opposite faces of the opening, the apparatus comprising:

a reference electrode coupled to the first side of the opening, the reference electrode being electrically connected to the system ground;

a first electronic driving circuit for generating an output signal related to a measured capacitance within the opening;

a sensor electrode coupled to a second side and being electrically connected to a first electronic driving circuit at a first connection;

a first resistor electrically connected between the first connection and a supply voltage;

a second electronic driving circuit;

a shield electrode coupled to the second side of the opening and being electrically connected to the second electronic driving circuit at a second connection;

a second resistor electrically connected between the second connection and the supply voltage; and a low pass filter circuit for generating a capacitance signal by filtering the output signal.

9. The apparatus according to claim 8, wherein the edge of a label on the label web is determined by sensing a change in the output signal greater than a threshold.

10. The apparatus according to claim 9, wherein the first electronic driving circuit is a first monostable multivibrator circuit having a first clock input.

11. The apparatus according to claim 10, wherein the second electronic driving circuit is a second monostable multivibrator circuit having a second clock input.

12. The apparatus according to claim 11, wherein the first clock input and the second clock input are electrically connected to a 2 MHz system clock signal.

13. The apparatus according to claim 8, wherein a first RC time constant is created by the first resistor and a first capacitance between the reference electrode and the sensor electrode, wherein a second RC time constant is created by the second resistor and a second capacitance between the reference electrode and the shield electrode, and wherein the second RC time constant is matched with the first RC time constant to minimize a mutual capacitance between the sensor electrode and the shield electrode.

14. A system for providing a capacitive label sensor having a reference electrode coupled to a first side of an opening in the sensor, a sensor electrode coupled to a second side of the opening such that an object passes between the reference electrode and the sensor electrode, and a shield electrode coupled to the second side of.the opening, the shield electrode surrounds the sensor electrode on the plane of the second side of the opening, the system comprising:

means for electrically connecting the reference electrode to a system ground;

means for electrically connecting the sensor electrode to a first end of a first resistor and a first electronic driving circuit at a first connection, the first resistor is electrically coupled between the first connection and a supply voltage;

means for electrically connecting the shield electrode to a first end of a second resistor and a second electronic driving circuit at a second connection, the second resistor is electrically coupled between the second connection and the supply voltage;

means for determining the edge of the object passing through the opening of the sensor by determining a change in capacitance between the reference electrode and the sensor electrode;

means for filtering the output signal using a low-pass filter to generate a capacitance signal; and means for determining a change in capacitance between the reference electrode and the sensor electrode by determining a change in the capacitance signal greater than a threshold value;

wherein the first electronic driving circuit is a first monostable multivibrator circuit having a clock signal input and generating an output signal;

the second electronic driving circuit is a second monostable multivibrator circuit having a clock signal input; and the first and second monostable multivibrator circuit clock signal inputs are electrically coupled to a system clock signal.

15. The system according to claim 14, wherein a first RC time constant is created by the first resistor and a first capacitance between the reference electrode and the sensor electrode, wherein a second RC time constant is created by the second resistor and a second capacitance between the reference electrode and the shield electrode, the system further comprising a means for matching the second RC time constant with the first RC time constant to minimize a mutual capacitance between the sensor electrode and the shield electrode.

* * * * *